United States Patent
Hall et al.

(10) Patent No.: US 11,679,386 B2
(45) Date of Patent: Jun. 20, 2023

(54) COMMINUTION OF FECES AND PREPARATION FOR ANALYSIS

(71) Applicant: Hall Labs, Inc., Provo, UT (US)

(72) Inventors: David R. Hall, Provo, UT (US); David Crismon, Herriman, UT (US); K. Jeffrey Campbell, Spanish Fork, UT (US); Joshua Larsen, Spanish Fork, UT (US); Anthony E. Pullen, Tucson, AZ (US)

(73) Assignee: Medic, Inc., Provo, UT (US)

( * ) Notice: Subject to any disclaimer, the term of this patent is extended or adjusted under 35 U.S.C. 154(b) by 430 days.

(21) Appl. No.: 16/869,467

(22) Filed: May 7, 2020

(65) Prior Publication Data

US 2020/0391204 A1    Dec. 17, 2020

Related U.S. Application Data

(60) Provisional application No. 62/986,651, filed on Mar. 7, 2020, provisional application No. 62/862,554, filed on Jun. 17, 2019, provisional application No. 62/862,569, filed on Jun. 17, 2019.

(51) Int. Cl.
| | | |
|---|---|---|
| *B01L 3/10* | (2006.01) | |
| *B01L 3/00* | (2006.01) | |
| *G01N 1/04* | (2006.01) | |
| *B01L 3/02* | (2006.01) | |
| *E03D 9/10* | (2006.01) | |
| *G01N 1/28* | (2006.01) | |

(52) U.S. Cl.
CPC ............ *B01L 3/5027* (2013.01); *B01L 3/021* (2013.01); *E03D 9/10* (2013.01); *G01N 1/04* (2013.01); *G01N 1/2813* (2013.01); *B01L 2300/0663* (2013.01); *B01L 2300/1805* (2013.01)

(58) Field of Classification Search
None
See application file for complete search history.

(56) References Cited

U.S. PATENT DOCUMENTS

| | | | |
|---|---|---|---|
| 9,867,513 B1 * | 1/2018 | Hall | A47K 13/24 |
| 2017/0260728 A1 * | 9/2017 | Hall | E03D 9/08 |
| 2018/0182367 A1 * | 6/2018 | Hall | G01N 29/28 |
| 2018/0371735 A1 * | 12/2018 | Hall | G01N 33/493 |

\* cited by examiner

*Primary Examiner* — Jyoti Nagpaul

(57) ABSTRACT

An analytical toilet comprising: a bowl for collecting feces from a user; a comminutor that comminutes at least a portion of the feces; a processing fluid driver that causes a processing fluid to mix with and transport at least a portion of the comminuted feces to an analytical station in the toilet; a separator that separates a sample of the at least a portion of the comminuted feces to be analyzed; and a wash fluid driver that causes a wash fluid to wash the feces out of the bowl.

20 Claims, 6 Drawing Sheets

COMMINUTION OF FECES AND PREPARATION FOR ANALYSIS

CROSS-REFERENCE TO RELATED APPLICATIONS

This application claims the benefit under 35 U.S.C. 119(e) of U.S. Provisional Patent Application No. 62/862,554 filed Jun. 17, 2019, U.S. Provisional Patent Application No. 62/862,569 filed Jun. 17, 2019 and U.S. Provisional Patent Application No. 62/986,651 filed Mar. 7, 2020. The disclosures of each of said applications are hereby incorporated herein by reference.

TECHNICAL FIELD

The present disclosure relates to toilets. More particularly, the present disclosure relates to analytical toilets equipped to provide health and wellness information related to excreta deposited by a user.

BACKGROUND

The ability to track an individual's health and wellness is currently limited due to the lack of available relevant data related to personal health. Many diagnostic tools are based on examination and testing of bodily fluids, such as blood, saliva, and excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Stool sample collection, preparation and analysis presents several challenges. Collecting and analyzing stool samples in an analytical toilet would address some of these challenges. Nevertheless, preparation of those stool samples collected in the toilet for analysis in the toilet presents several other challenges. For example, stool samples can come in many forms, most of which are not amenable to typical analytical equipment design and analysis methods.

SUMMARY

One aspect of the present invention is an analytical toilet that includes a bowl for collecting feces from a user, a comminutor that comminutes at least a portion of the feces, and a processing fluid driver. The processing fluid driver causes a processing fluid to mix with and transport at least a portion of the comminuted feces to an analytical station in the toilet. The analytical toilet further includes a separator that separates a sample of the at least a portion of the comminuted feces to be analyzed, and a wash fluid driver that causes a wash fluid to wash the feces out of the bowl.

In another aspect, the processing fluid driver includes a fluid jet, nozzle, microfluidic, capillary, diaphragm, piston, screw, rotary, or a peristaltic dispensing system.

Instill another aspect, the analytical toilet further includes a cover that separates the comminutor from the bowl.

In a still further aspect, the analytical toilet further includes a filter between the comminutor and the analytical station. The filter can be a disk filter. A sample can be moved to the analytical station through a microfluidic channel.

In another aspect of the present invention, the comminutor in the analytical toilet can be an auger, an emulsifier, a masticator, a sonicator, a homogenizer, high pressure fluid, a mill, blender, Dounce homogenizer, Potter-Elvehjem homogenizer, French press, or a grinder, or a combination thereof.

In still another aspect, the processing fluid can be water together with at least one of a buffer, a reducing agent, a protease inhibitor, an osmolyte, an ionic stabilizer, or an α-helix stabilizer.

In a still further aspect, the separator in the analytical toilet can be a pipette.

In a yet still further aspect, the analytical toilet can further include an imaging sensor for capturing images of the comminuted feces. A channel may be included such that a portion of the comminuted feces passes through, thereby producing a thin layer of comminuted feces, and where the imaging sensor is on one side of the thin layer of comminuted feces and a light source is on the other side of the thin layer of comminuted feces.

In another aspect of the present invention, the imaging sensor further includes a processor that processes images captured by the imaging sensor to thereby recognize parasites, parasite larva, parasite eggs, bacteria or viruses. Specifically, the processor is capable of recognizing images of one or more of cryptosporidium, microsporidia, and isospora, tapeworms, flukes, Fasciolopsis buski, hookworms, microsporidia, whipworms, protozoa, Balantidium coli, Dientamoeba fragilis, Encephalitozoon hellem, Necator americanus, heterophyes heterophyes, Metagonimus yokogawai, pinworms, trichinosis worms, Giardia intestinalis, Giardia lamblia, Entamoeba histolytica, Cyclospora cayetanenensis, ascarias lumbricoides, strongyloidiasis, Ancylostoma duodenale, Taenia, Cystoisospora belli, Diphyllobothrium, Hymenolepsis, Echinococcus, Dipylidium, Spirometra, Enterobius vermicularis, and Cryptosporidium.

In still another aspect of the present invention, the analytical station in the analytical toilet includes a slide warmer.

In a still further aspect, the analytical station in the analytical toilet includes a dispenser that dispenses a stain, a fixative, a reagent, or combinations thereof. One or more stains can include eosin/saline, acridine orange, auramine phenol, Field's stain solution A and B, Giemsa stain, Lugol's iodine, iron haematoxylin solution A and B, trichrome for microsporidia, trichrome for protozoa, malachite green, methylene blue, Gram's fuchsin, safranin O, Gram's iodine, crystal violet, or Kinyoun's Carbol fuchsin.

In a yet still further aspect, an analytical toilet for collecting, analyzing, and disposing of feces includes a bowl for collecting feces from a user, a source of acoustic energy directed at the feces and having sufficient intensity to comminute the feces to an extent sufficient to produce comminuted feces, and a source of flush water to wash the comminuted feces out of the bowl.

In still yet another aspect, the analytical toilet further includes an imaging sensor for capturing images of the comminuted feces. A channel may further be included through which a portion of which comminuted feces passes, thereby producing a thin layer of comminuted feces, and where the imaging sensor is on one side of the thin layer of comminuted feces and a light source is on the other side of the thin layer of comminuted feces. A processor can be further included for processing images from the imaging sensor, and to recognize images of one or more parasites.

Further aspects and embodiments are provided in the foregoing drawings, detailed description and claims. Unless specified otherwise, the features as described herein are combinable and all such combinations are within the scope of this disclosure.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Overview

Figure 1A:
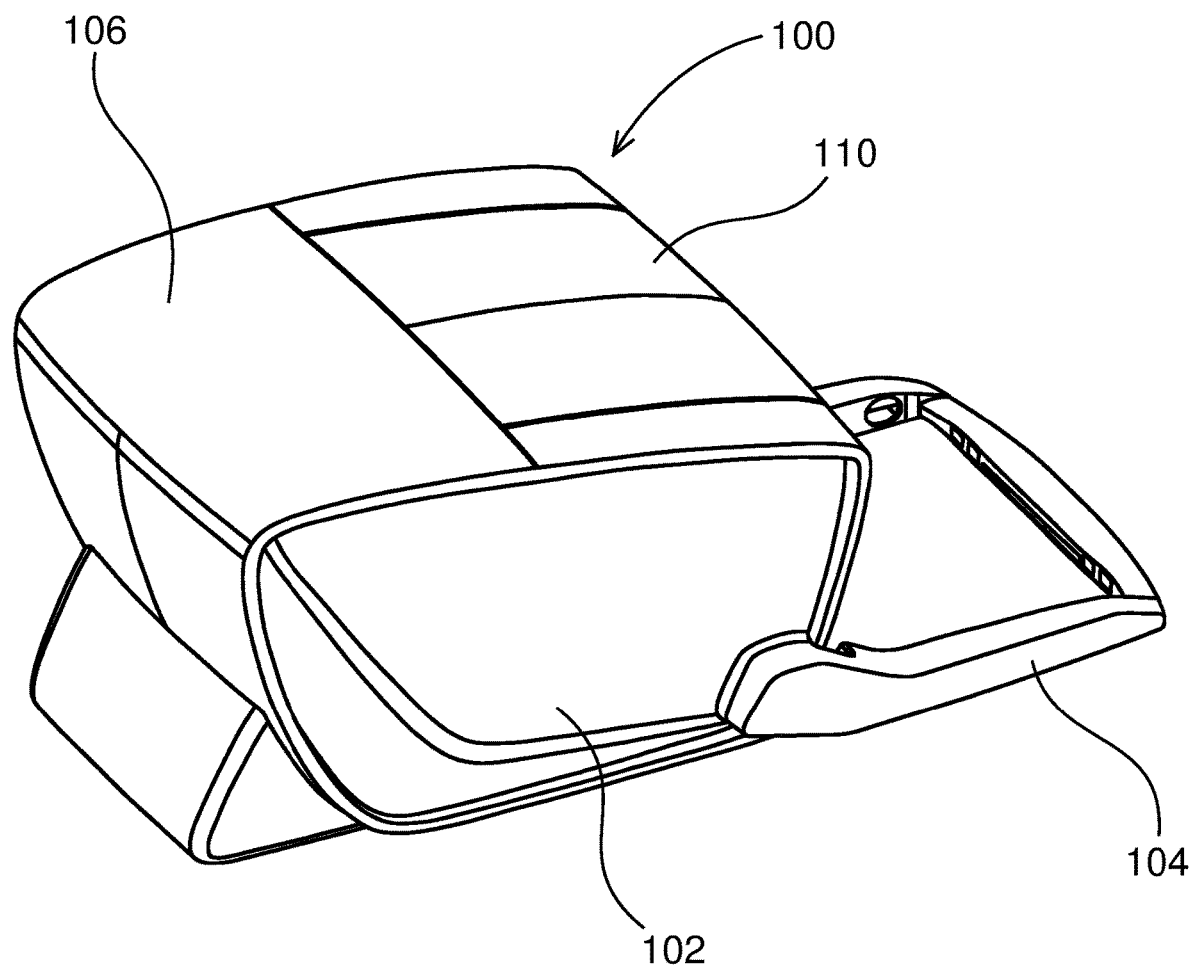
FIG. 1A illustrates an analytical toilet with the lid closed, according to an embodiment of the disclosure.

Embodiments of methods, materials and processes described herein are directed towards analytical toilets. Analytical toilets are equipped to provide health and wellness information related to excreta deposited by a user.

Analytical toilets can be used to analyze feces excreted by a user. The disclosure herein describes a system to comminute feces and prepare the feces for analysis. Various components of the system are described such as devices to comminute a sample of feces, devices to dispense one or more processing fluids to the feces, and analytical methods to evaluate the sample of feces.

Definitions

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the term "excreta" refers to any substance released from the body including urine, feces, menstrual discharge, saliva, mucus, expectorate, sputum, and anything contained or excreted therewith. The term "solid excreta" specifically refers to feces, even when the feces is in a more liquid or watery state, as when a user is suffering from diarrhea or gastroenteritis.

As used herein, the term "manifold" is intended to have a relatively broad meaning, referring to a device with multiple conduits and valves to controllably distribute fluids, namely water, liquid sample and air.

As used herein, the term "microfluidics" is meant to refer to the manipulation of fluids that are contained to small scale, typically sub-millimeter channels. The "micro" used with this term and others in describing this invention is not intended to set a maximum or a minimum size for the channels or volumes.

As used herein, the term "microfluidic chip (MFC)" is meant to refer to is a set of channels, typically less than 1 $mm^2$, that are etched, machined, 3D printed, or molded into a microchip. The micro-channels are used to manipulate microfluidic flows into, within, and out of the microfluidic chip.

As used herein, the term "microfluidic chamber" is meant to refer to a test chamber adapted to receive microfluidic flows and/or a test chamber on a microfluidic chip.

As used herein, the term "lab-on-chip" is meant to refer to a device that integrates one or more laboratory functions or tests on a single integrated circuit. Lab-on-a-chip devices are a subset of microelectromechanical systems (MEMS) and are sometimes called "micro total analysis systems" (µTAS).

As used herein, a "fluidic chip" is meant to refer to a physical device that houses a fluidic circuit. Often, a fluidic chip facilitates the fluid connection of the fluidic circuit to a body of fluid.

As used herein, the prefix "nano-" is meant to refer to something in size such that units are often converted to the nano-scale for ease before a value is provided. For example, the dimensions of a molecule may be given in nanometers rather than in meters.

As used herein, the term "comminute" is meant to have a relatively broad meaning, referring to the process of making smaller pieces out of bigger pieces. In the context of the present invention, the feces deposited in the toilet can be comminuted by various methods so as to make it easier to analyze and/or further process.

As used herein, the term "auger conveyor" is meant to refer to a mechanism that uses a rotating helical screw blade, called a "flighting", usually within a tube, to move liquid or solid granular materials. Auger conveyors usually consist of a trough or tube containing either a spiral blade coiled around a shaft, driven at one end and held at the other, or a "shaftless spiral", driven at one end and free at the other. The rate of volume transfer is proportional to the rotation rate of the shaft.

As used herein, "biomarker" and "biological marker" are meant to refer to a measurable indicator of some biological state or condition, such as a normal biological processes, pathogenic processes, or pharmacologic responses to a therapeutic intervention. Some biomarkers are related to individual states or conditions. Other biomarkers are related to groups or classifications or states or conditions. For example, a biomarker may be symptomatic of a single disease or of a group of similar diseases that create the same biomarker.

Exemplary Embodiments

The present disclosure relates to methods to comminute feces. There are several methods that may be used to comminute a sample of feces for preparation to be analyzed by one or more analytical methods. One comminution method is the use of one or more streams of a pressurized fluid such as water. This forms a comminuted sample of feces.

Figure 1B:
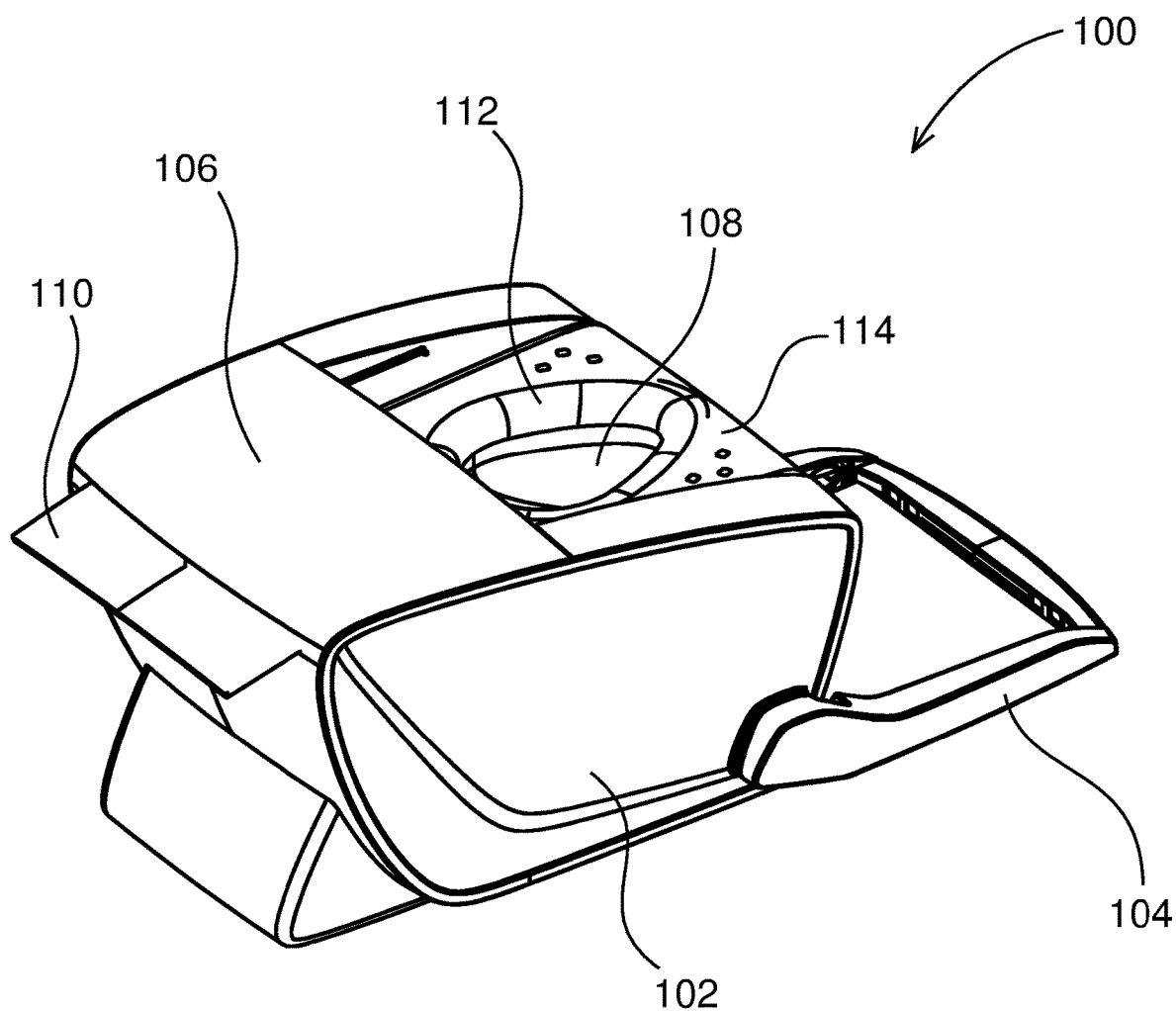
FIG. 1B illustrates an analytical toilet with lid open, according to an embodiment of the disclosure.
Figure 1C:
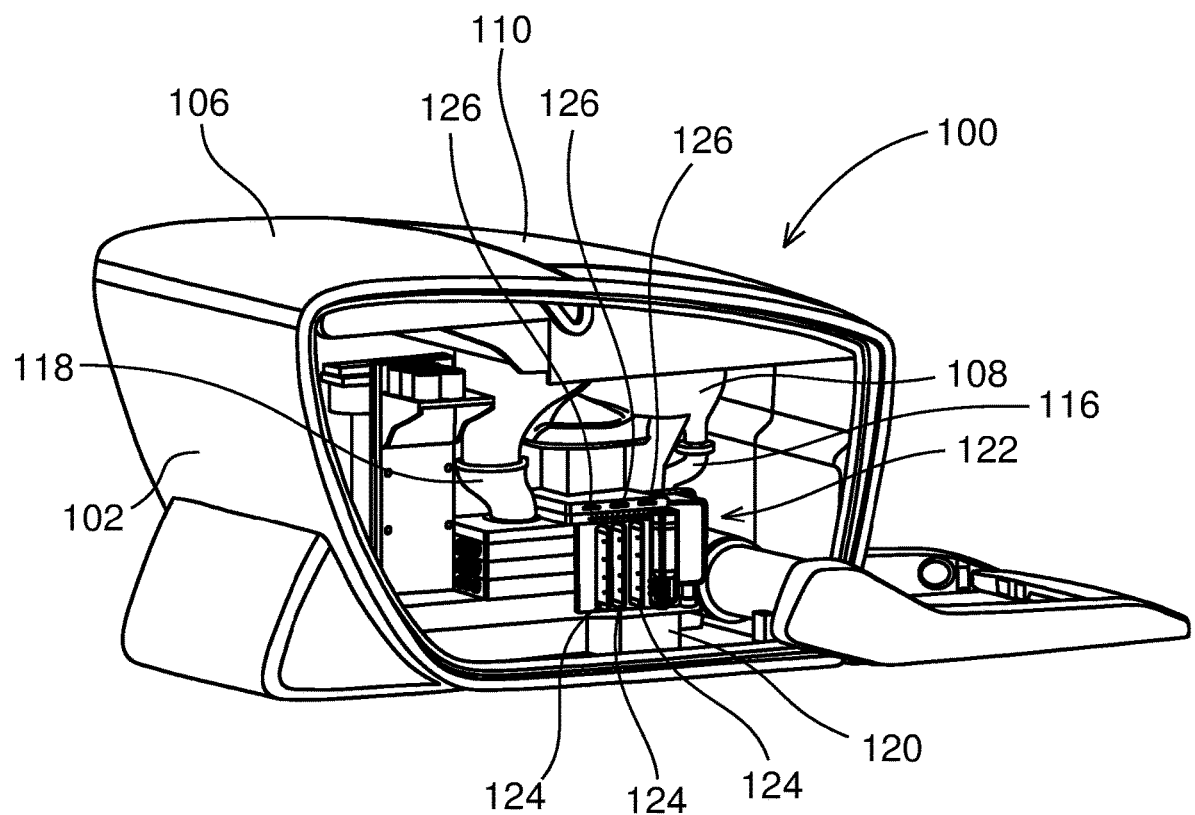
FIG. 1C illustrates an analytical toilet with lid closed and a portion of the exterior shell removed, according to an embodiment of the disclosure.

Now referring to FIGS. 1A-C, a preferred embodiment of an analytical toilet 100 is shown. FIG. 1A illustrates the analytical toilet 100 with the lid 110 closed, according to an embodiment of the disclosure. FIG. 1A further shows exterior shell 102, foot platform 104 and rear cover 106. The lid 110 is closed to prevent a user from depositing urine in toilet 100 until the toilet is ready for use.

FIG. 1B illustrates toilet 100 with lid 110 open, according to an embodiment of the disclosure. Toilet 100 includes exterior shell 102, rear cover 106, bowl 108, seat 112, lid 110, fluid containers 114 and foot platform 104. Housed within toilet 100 are a variety of features, including equipment, that facilitate receiving excreta, processing urine for analysis, analyzing urine, and disposing of urine. FIG. 1B shows toilet 100 with lid 110 open so a user can sit on seat 112 and deposit excreta in toilet 100.

FIG. 1C illustrates toilet 100 with lid 110 closed and a portion of exterior shell 102 removed, according to an embodiment of the disclosure. This allows access to equipment housed within toilet 100. With exterior shell 102 removed, base 120, urine collection pipe 116, feces collection pipe 118, and manifold area 122 is visible. Urine collection pipe 116 further comprises a passageway to deliver a urine sample to the manifold area 122 and to a detection system. Manifold area 122 includes test areas 124 and fluidic chip slots 126. Preparation and/or analysis of sample can selectively take place in a test area 124 or fluidic chip slot 126. Manifold area 122 is the area where analysis takes place. A filter may be added over the entrance of the urine collection pipe 116 to prevent solid material, such as feces or toilet paper, from entering the pipe.

A manifold 122 is located below the bowl 108. The manifold 122 comprises a plurality of fluid paths. These fluid paths allow the manifold 122 to move fluids between the bowl 108, fluid containers 114, outside sources (e.g., municipal water supplies), other sources (e.g., air or water electrolyzing unit), analytical test devices 124, and the toilet outlet. The analytical test devices 124 make up a detection system for one or more viruses. The manifold 122 also provides electrical power and data connections to the analytical test devices 124. The manifold 122 can also directly pass fluids and/or solids from the bowl 108 to the toilet outlet. The manifold 122 is adapted to provide receptacles 124 with standardized connection interfaces for multiple analytical test devices 124. The manifold 122 may comprise multiple fluid sources for the analytical test device 124. In various embodiments, the manifold 122 may include receptacles for more than one type of analytical test device 124 (e.g., different sizes, fluid supply needs, etc.). In various exemplary embodiment, the analytical test device 124 includes multiple inlets in fluid communication with the manifold 122. The analytic test device 124 may also include at least one outlet or drain in fluid communication with the manifold 122.

In various exemplary embodiments, manifold 122 may comprise a microfluidic system to isolate and transport a sample, add and mix reagents if appropriate, filter out solids, and test the sample for one or more coronaviruses on a small scale (i.e., sub-millimeter scale) in a health and wellness analytical toilet described herein. The microfluidic system may comprise an open microfluidic system, continuous-flow microfluidic system, droplet-based microfluidic system, digital microfluidic system, nanofluidic system, paper-based microfluidic system or combinations thereof. The microfluidic system may be used to introduce and feed fluidic samples into paper-based immunoassay test strips, cartridges or cassettes.

In various exemplary embodiments, an MFC is designed to use very small quantities of reagent. In various exemplary embodiments, reagents are dispensed using technology similar to that used in inkjet printers to dispense ink. In some embodiments, an electrical current is applied piezoelectric crystal causing its shape or size to change forcing a droplet of reagent to be ejected through a nozzle. In some embodiments, an electrical current is applied to a heating element (i.e., resistor) causing reagent to be heated into a tiny gas bubble increasing pressure in the reagent vessel forcing a droplet of reagent to be ejected.

In various exemplary embodiments, the toilet fluidic manifold 122 provides routing. Interconnecting levels of channels allows routing from one port to all others. Each channel includes an accumulator; allows for constant pressure pumping of all active channels simultaneously, while time-multiplexing pump-driven inflow.

In various exemplary embodiments, the manifold has reaction chambers built in for general purpose mixing and filtering operations. Each chamber has a macro-sized channel through which the manifold delivers a sample extracted from urine (filling the reaction chamber), and the chamber has a micro-sized channel. Pumps located internal or external to the manifold drive fluid into the reaction chamber, and into the micro-sized channel. A valve at the output of the macro-channel, and possibly at the output of the micro-channel, controls fluid direction as it exits the reaction chamber.

Microfluidic applications require support infrastructure for sample preparation, sample delivery, consumable storage, consumable delivery or replenishment, and waste extraction. In various exemplary embodiments, the manifold includes integrated support for differential pressure applications, pneumatic operations, sample and additive reservoirs, sample accumulators, external pumps, pneumatic pressure sources, active pump pressure (e.g., peristaltic, check-valve actuators, electro-osmotic, electrophoretic), acoustic or vibrational energy, and light-interaction (e.g., spectrometer, laser, UV, magnification). The acoustic energy source may be a high frequency bulk acoustic wave (BAW) actuator.

In various exemplary embodiments, the manifold interface has a matrix of ports, possibly laid out in a regular grid. These ports may be activated or closed via an external support manifold. Routing is fully programmable.

In various exemplary embodiments, the manifold 122 directs one or more fluids to the analytical test device 124 or an MFC analytical test device to cleanse the devices. These may include cleaning solutions, disinfectants, detergents, and flushing fluids. In various exemplary embodiments, the manifold directs hot water or steam to clean sample, reagents, etc. from the devices. In various exemplary embodiments, the toilet systems using oxygenated water, ozonated water, or electrolyzed water, any of which may be generated on an as-needed basis by the toilet system (this may be internal or external to the toilet).

In various exemplary embodiments, waste from the MFCs is managed based on its characteristics and associated legal requirements. Waste that can be safely disposed is discharged into the sewer line. Waste that can be rendered chemically inert (e.g., heat treatment, vaporization, neutralization) is processed and discharged. Waste that cannot be discharged or treated in the toilet system is stored, and sequestered if necessary, for removal and appropriate handling.

In various exemplary embodiments, the manifold creates sequestered zones for each of these waste categories and ensures that all products are properly handled. In various exemplary embodiments, the manifold directs flushing water and/or cleansing fluids to clean the manifold and MFC. In some embodiments, high-pressure fluids are used for cleaning. In such an embodiment, the high-pressure fluids are not used in the MFC. In some embodiments, the MFC is removed from the backplate interface and all ports are part of the high-pressure cleansing and/or rinse.

Figure 2:
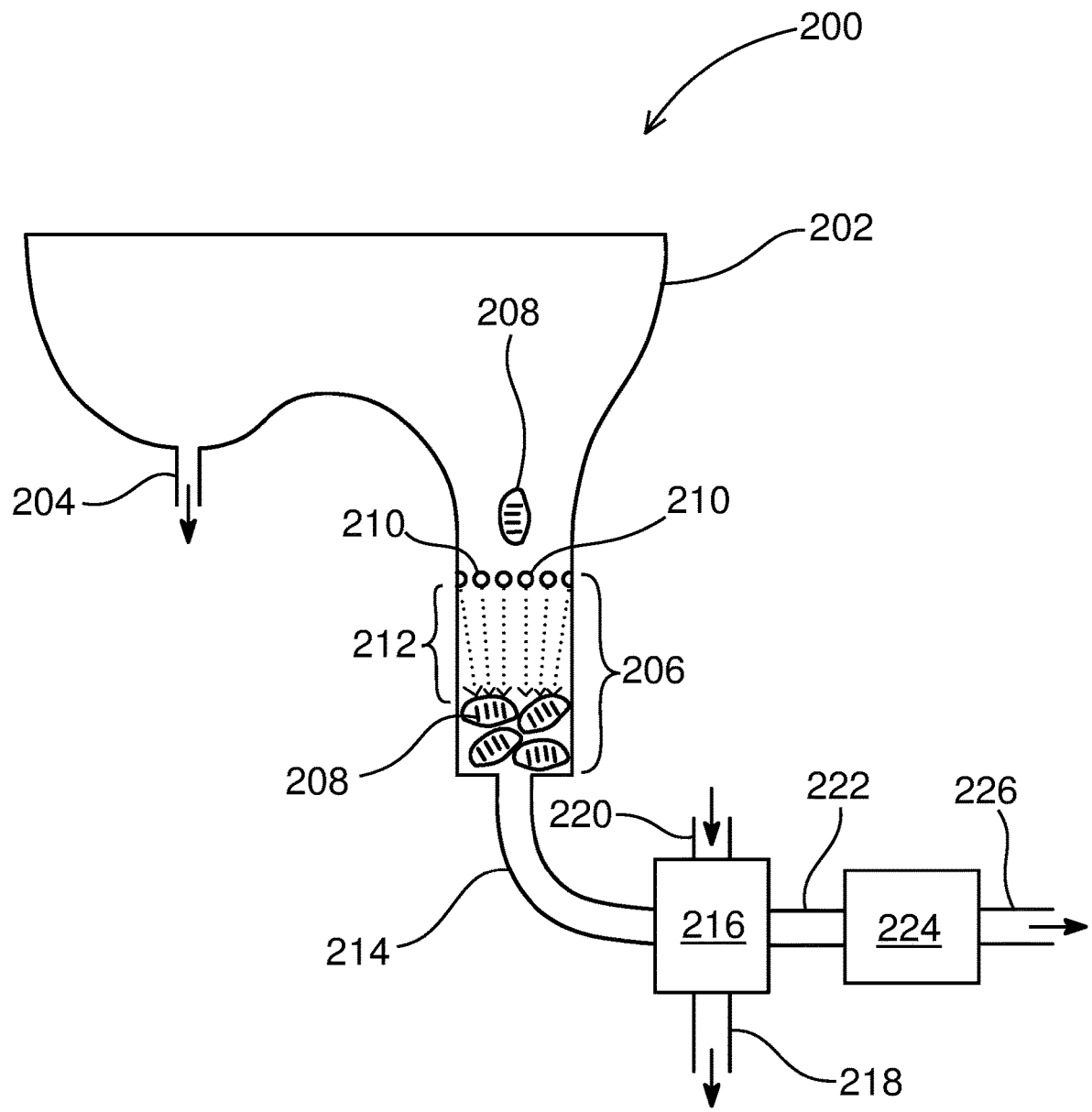
FIG. 2 illustrates a cross-section of a design of a portion of an analytical toilet capable of comminuting feces, according to an embodiment of the disclosure.

FIG. 2 illustrates a cross-section of a design of a portion of an analytical toilet capable of comminuting feces 200, according to an embodiment of the disclosure. Analytical toilet 200 comprises a bowl 202 to receive excreta. Toilet 200 further comprises a first drain 204 to receive urine. The first drain 204 may be used to move urine to a sensor or other location for further processing and analysis. First drain 204 may be in fluidic communication with a sewer. Toilet 200 further comprises a chamber area 206, such as a receptacle, or a reservoir, where feces 208 settles after being deposited by a user. Chamber 206 may further comprise a lid or cover that separates the bowl 202 from the chamber 206 wherein a comminutor device is located. The lid or cover may be mechanical in nature that automatically closes or covers chamber 206 upon sensing the presence of feces. The cover may close upon activation by a user once the user is finished leaving a sample of feces and before a comminution process begins. This may prevent splash back into the bowl during a comminuting process.

Once excreta 208 is in the chamber 206, one or more fluid jets, dispensers, or nozzles 210 may emit a controlled stream of a fluid 212 towards the feces 208. The stream rate and volume of the emitted fluid may be controlled. For example, a high pressure stream of fluid 212 may be emitted to act as a comminutor in a comminuting process to comminute the feces 208. A fluidized state of the feces may be formed. The fluid 212 may comprise water, a buffer, a reducing agent, a protease inhibitor, an osmolyte, an ionic stabilizer, or an α-helix stabilizer.

Analytical toilet 200 may comprise a processing fluid driver. The processing fluid driver may comprise additional dispensing units that may be integrated into analytical toilet 200 to dispense water, a buffer, a reducing agent, a protease inhibitor, an osmolyte, an ionic stabilizer, an α-helix stabilizer, or other reagents to further process the feces sample to prepare for analysis. The dispensing system of the processing fluid driver may comprise a microfluidic, capillary, diaphragm, piston, screw, rotary, or peristaltic dispensing system. Once a sufficient amount of fluid has been emitted and a desired consistency has been attained, at least a portion of the comminuted feces mixture may then be moved by the processing fluid driver and separated with a separator or separating device for further processing or analysis by a second drain 214. Once the portion of comminuted feces is drained, a wash fluid driver may then emit a wash fluid from nozzles 210 or other nozzles to remove any remaining feces and may further clean and sanitize chamber 206 in preparation of another feces sample.

Drained comminuted feces may then be passed through a filter 216. Filter 216 may comprise a screen, sieve, surface filter or depth filter. Filter 216 may be replaceable either manually or automatically. Filter 216 further comprises a drain 218 to remove filtered particulates that are washed out using a stream of fluid from inlet 220. Drain 218 may lead to a trap and a sewer pipe. Another separating device may be integrated with filter 216. For example, a separating device to extract a sample may be employed such as an autopipette system. The autopipette system can extract a substantially precise amount (i.e., aliquot) of comminuted feces for testing and analysis. The sample extraction device may extract liquidized feces samples greater than about 0.014 for analysis. The sample extraction device may extract liquidized feces samples in the range of about 0.014 to about 5 ml for analysis.

Filtered fluid that passes through filter 216 is drained via outlet 222 and moved toward analytical station 224. This may be completed by the processing fluid driver. The analytical station 224 comprises one or more sensing devices. The filtered fluid is drained out of analytical station 224 using outlet 226 that may lead to a trap and a sewer pipe. Further fluid from nozzles 210 may be needed to be emitted to aid in washing the comminuted feces toward a drain/sewer pipe. In a preferred embodiment, analytical station 224 comprises an image sensor. Bowl 202, chamber 206, drain 214, filter 216, outlet 222, analytical station 224, outlet 226 and a sewer pipe are in fluidic communication.

Another method of comminution includes the use of an auger conveyor. An auger conveyor, also known as a "screw conveyor", has one or more rotating helical screw blades. An example of this is the Archimedes screw. When placed inside a cylindrical space with approximately the same diameter as the outside edge of the screw, material will be forced along one direction of the axis of rotation by the rotating blades. The cylindrical space may comprise a tube with an inner diameter in the range of about 1-5 cm. The screw diameter may be about 0.5-2 mm less than the inner diameter of the cylindrical space. The auger screw may rotate at a rate in a range of about 1-60 revolutions/min. Chamber 206 in toilet 200 may further comprise an auger. The auger may be located at the bottom of chamber 206 in order to receive feces and a fluid. An auger may operate as a masticator. One type of auger is a masticating auger. A masticating auger comprises a single auger to compact and crush material into smaller sections before squeezing out moisture along a static screen while the solid material is expelled through a separate outlet.

Another method of comminution of feces is emulsification. Emulsification is the process forming a substantially homogenous mixture from two or more substances that are typically immiscible. Typically, feces forms an immiscible mixture with a fluid such as water. By breaking up the feces into small, fine particles, the particles may be suspended in the fluid in a homogenous, fluidized manner such that the mixture appears uniform. Physical emulsification methods to achieve a substantially homogenous mixture of feces in water includes a blender, such as a Waring blender. A mill may also be used such as a planetary or attrition mill. In some instances, a surfactant may be added to stabilize the formed emulsion. An emulsifier may be located in chamber 206.

Another method of comminution of feces that may be used is sonication. Sonication is the process of applying acoustic energy to agitate particles in a sample. Sonication typically uses ultrasonic frequencies greater than about 20 kHz. Agitation may cause break up the larger particles into smaller particles. Chamber 206 in toilet embodiment may further comprise a sonicator. Acoustic waves can be directed at the feces mass from above, from the sides and/or from below and will cause the mass to disintegrate and become more effectively imaged and tested. The acoustic waves used in the present invention can be generated by conventional means. Typically, for applications such as this the acoustic waves are generally a low frequency. Preferably in the range between about 20 kHz and about 100 kHz. Most preferably, the frequency is in the range of about 20-50 kHz. Higher frequencies may also be used in the range of about 100 kHz to about 1 GHz. For example, chamber 206 may be configured with a high frequency (~54 MHz) bulk acoustic wave (BAW) actuator.

Another method of comminution of feces that may be used is ultrasonic vibration milling. An ultrasonically vibrating mill utilizes high frequency, low amplitude vibrations. The transducer in the mill may comprise a piezoelectric transducer (piezoelectric grinding/machining) or a magnetorestrictive transducer. Chamber 206 in toilet embodiment 200 may comprise an ultrasonic vibration mill.

Another method of comminution of feces is the use of high pressure grinding. High pressure grinding relies on the material being grinded to be passed through high pressure grinding rolls. A high-pressure grinder may be located in or near chamber 206.

Other methods of comminution of feces may include a Dounce homogenizer, Potter-Elvehjem homogenizer, French press, a crusher, a shredder, agitator or a grinder.

Figure 3:
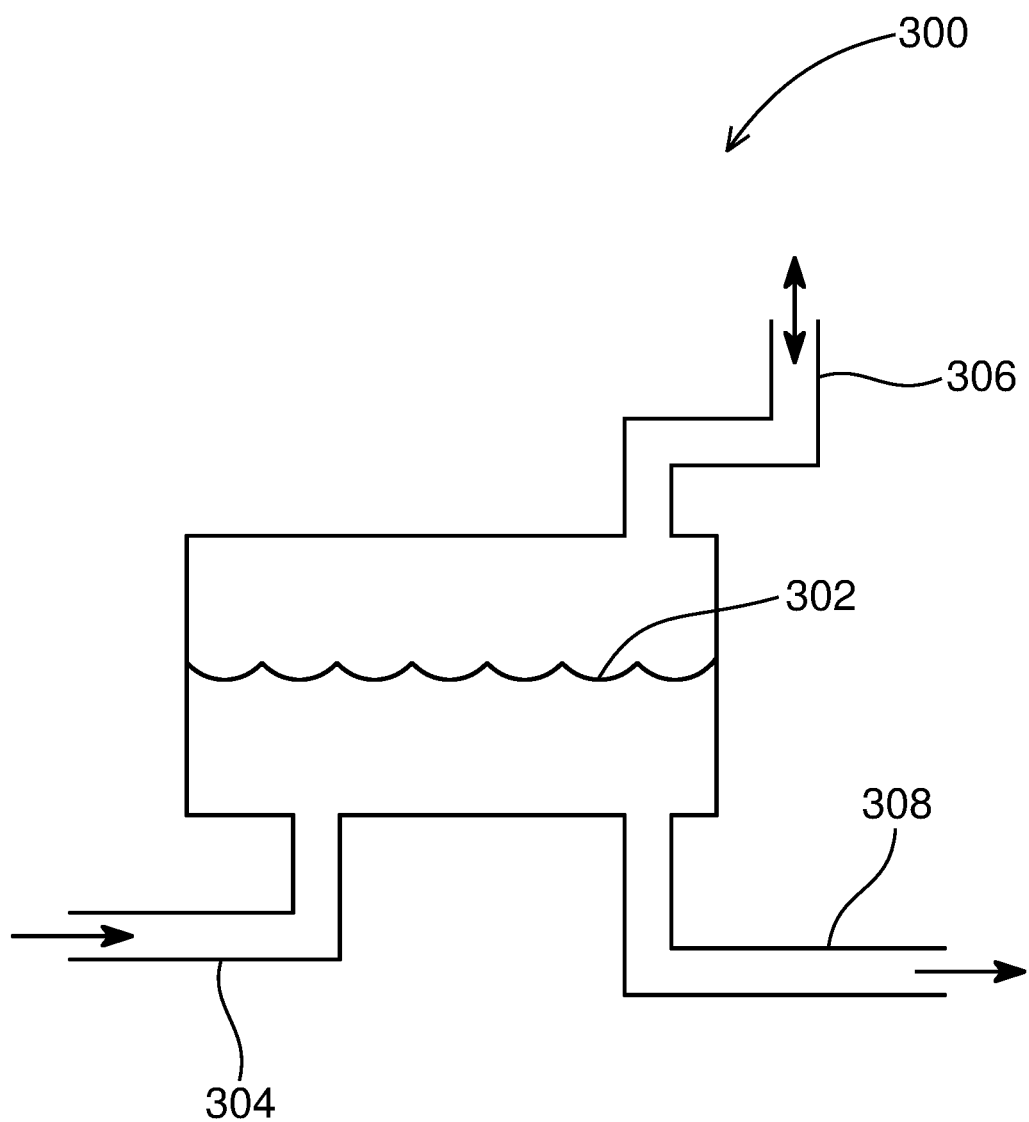
FIG. 3 illustrates a chamber, according to an embodiment of the disclosure.

Any of the comminution methods described herein may take place in chamber 206. FIG. 3 illustrates a chamber 300, according to an embodiment of the disclosure. FIG. 3 shows an upstream sample chamber which delivers fluid to a manifold. The chamber 300 can be pressurized as fluid 302 enters from the bottom left of the chamber inlet 304 and can be pressurized to get it to the chamber. The chamber can be vented and/or pressurized from the top 306, and the fluid leaves the chamber from the bottom through outlet 308.

Following comminution, some particulates of the feces may exceed a preferred maximum size. Therefore, any method may be followed up with a second filter to separate particulates that pass through the filter from those that do not. Filters come in a variety of shapes, sizes, and materials. The selection of each filter property depends on the desired application within the toilet, including the size of particulate desired, whether specific chemical filtering is desired, any chemicals the filter may come in contact with the geometry of the area where the filter will go, the desired flowrate and pressure. The size of particle allowed through the filter will depend on a number of parameters, including the size of the sample or foreign body desired for subsequent processes or analysis and the size of material pathways a sample will subsequently pass through. This filtering can be achieved in many ways, including a single layer filter surface with perforations or openings sized to allow the desired sized particles through and prevent larger particles from getting through. Another type of filter may be a multi-stage filter with either filter layers where the openings in the filters are offset from each other or the openings get progressively smaller. Once filtered, the particulates on either side of the filter can be selectively processed for analysis, analyzed, and/or discarded.

Polypropylene blend filters may be used as a filter in analytical toilet embodiment 200. The polypropylene blend filters come in various density. Such filters may be a very coarse, open weave filter for good for high flow applications, coarse, semi-open weave that allows good flow but filters well, medium, fairly dense weave that traps a lot of debris and allows for medium flow and a fine, dense weave that results in lower flow but thorough filtration.

Other filters that may be used are stainless steel sintered filter disks (may include a Viton o-ring). Filter thresholds of 0.2, 0.5, 1, 2, 5, 10, 20, 40, and 100 microns may be used. Filters may be made from forming a cake out of stainless steel powder and then sintering it to bond the powder into an open matrix material. Disk filters may be made from woven or sintered mesh configuration, such as a wire screen, instead of sintered powder. These types of filters may be referred to as a "sieve". The mesh size may be a No. 4-8, 10, 12, 14, 16, 18, 20, 25, 30, 35, 40, 45, 50, 60, 70, 80, 100, 120, 140, 170, 200, 230, 270, 325 or 400.

Figure 4:
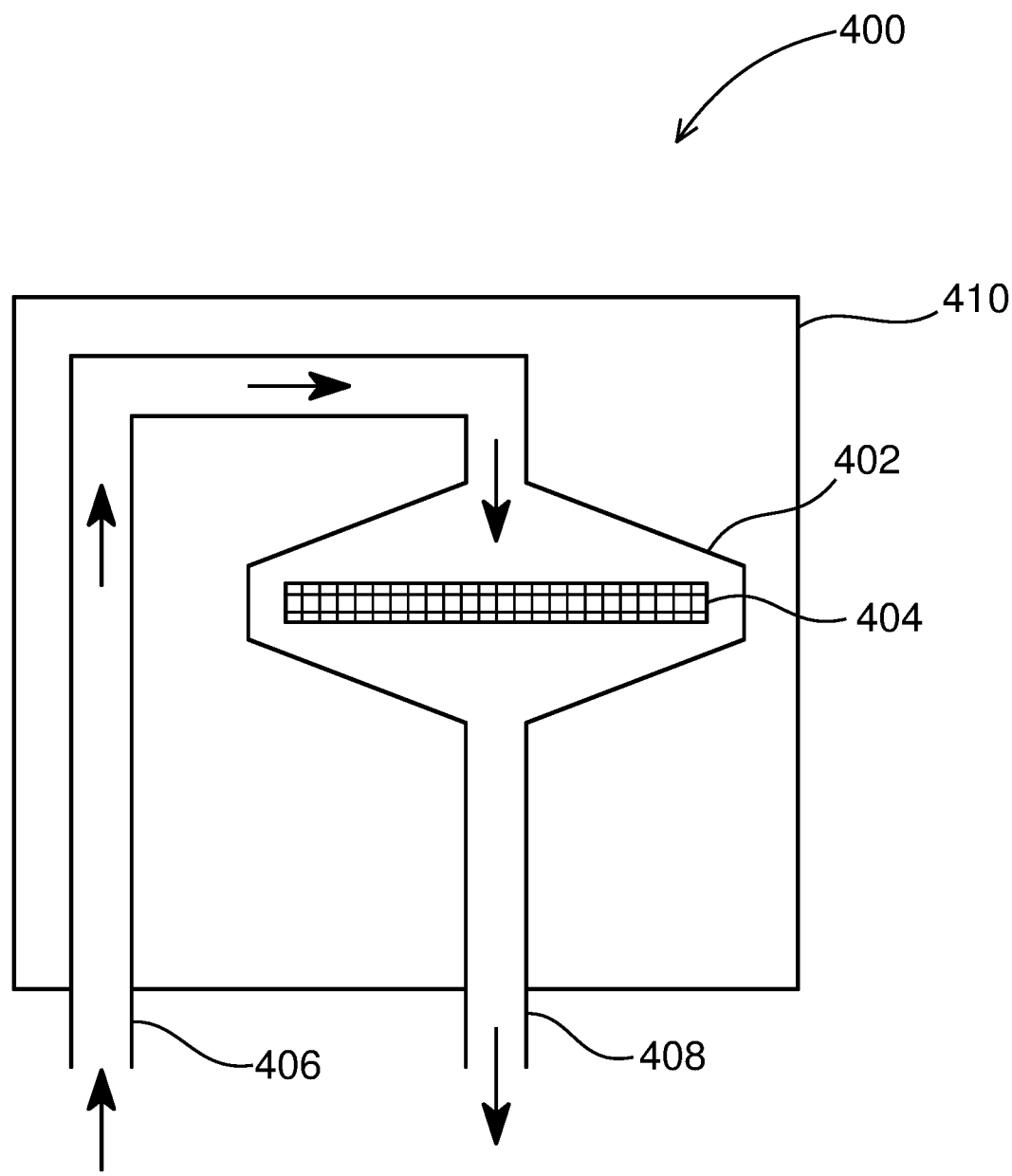
FIG. 4 illustrates a filter system, according to an embodiment of the disclosure.

FIG. 4 illustrates a filter system 400, according to an embodiment of the disclosure. FIG. 4 shows a manifold 402 with a disk filter 404 in a housing 410. In one preferred embodiment, all of these components are stainless steel. In another preferred embodiment, some or all of these materials are made from other metals, plastics, glass, or other materials and composites. The manifold 402 may be made from two or more pieces and can be joined together using clamps, screw connections or other methods. Fluid enters the manifold 404 from the bottom left through inlet 406. Liquid passes through the disc filter 404 and the filtered particles exit from the bottom center. In one preferred embodiment, the fluid entering the manifold is pressurized and the fluid leaving the manifold through outlet 408 is pulled by a vacuum. One preferred filter is a 2 micron filter. The filter 404 can be cleaned by reversing the flow direction and sending a fluid, such as water, through the filter, following which, water may flow in the normal direction to clean out any particles from the water that may have been captured by the underside of the filter. Another method may be to apply a high pressure pulse of a fluid in the opposite direction in order to clear the filter of material that may be wedged or lodged in the filter mesh.

In a preferred embodiment, the comminuted feces material may be flattened and then be analyzed, for example, by imaging with one or more cameras in analytical station 224. The feces sample may be deposited on a slide. By comminuting the originally deposited mass of feces, a thin layer of the feces may be much easier to form and analyze through imaging. The feces sample may be dried using a slide warmer or other device. Analysis may include the discovery of parasite larvae or eggs. The presence of a parasite may be considered a biomarker indicative of an infection or disease. The flattening procedure may include placing a sample of the comminuted feces material in a dropwise manner onto a surface, such as a glass slide, and allowing the material to spread out. Comminuted feces material may be placed into a cuvette. When analysis is not being carried out, the flattening procedure can be reversed to allow better flow to remove the tested feces and allow a new sample to arrive for analysis.

In some embodiments, the comminuted feces may be dried with a heating device. Dried or heated comminuted feces may be combined with one or more of a stain, a fixative or a reagent from a dispensing system. The dispensing system may comprise a microfluidic, capillary, diaphragm, piston, screw, rotary, or peristaltic dispensing system. A comminuted fecal sample may be stained with one or more stains to aid in further identification of bacteria, viruses, fungi, spores, or parasites. Some stains include eosin/saline, acridine orange, auramine phenol, Field's stain solution A and B, Giemsa stain, Lugol's iodine, iron haematoxylin solution A and B, trichrome for microsporidia, trichrome for protozoa, malachite green, methylene blue, Gram's fuchsin, safranin O, Gram's iodine, crystal violet or Kinyoun's Carbol fuchsin. A comminuted fecal sample may be combined with a fixative such as apafix, formalin, sodium acetate acetic acid formalin (SAF), merthiolate-iodine formalin (MIF), or polyvinyl alcohol (PVA). A comminuted fecal sample may be combined with a reagent such as Mayer's glycerine-albumin, Triton X-100 solution, neutral red, ethyl acetate, or acetone.

An image inspection system may be used to detect abnormalities in a sample of solid excreta. An image system may comprise a transducer. Some image inspection systems may include KEYENCE (Itasca, Ill., USA), INSPECT.Assembly™ (Radiant Vision Systems, Redmond, Wash., USA) or Lake Image Systems (Tring, Hertfordshire, United Kingdom). An image inspection sensor provides a visual sensor for the presence of parasites, blood, consistency, etc. An image inspection system may comprise one or more cameras and may provide 2D or 3D images. The image system may incorporate optical lenses for magnification of the sample, and light sources to supply illumination from above or below the sample. The image system may incorporate various optical filters to enhance the visibility of sample targets, or specific features of interest. The image system may comprise an image processor. The image processor may be capable of parallel computing. The image processor may be capable of Bayer transformation, noise reduction, demosaicing or image sharpening. The image processor may be a system on a chip with multi-core processor architecture. The image processor may be capable of processing image data and detecting and recognizing a parasite.

The image system may detect movement, such as from a living parasite larvae. Such parasites may include protozoan (i.e., single-celled parasites), such as cryptosporidium, microsporidia, and isospora. The parasites may also include parasitic worms (helminths), such as tapeworms, flukes, Fasciolopsis buski, hookworms, microsporidia, whipworms, protozoa, Balantidium coli, Dientamoeba fragilis, Encephalitozoon hellem, Necator americanus, heterophyes heterophyes, Metagonimus yokogawai, pinworms, trichinosis worms, Giardia intestinalis, Giardia lamblia, Entamoeba histolytica, Cyclospora cayetanenensis, ascarias lumbricoides, strongyloidiasis, Ancylostoma duodenale, Taenia, Cystoisospora belli, Diphyllobothrium, Hymenolepsis, Echinococcus, Dipylidium, Spirometra, Enterobius vermicularis and Cryptosporidium. The image system may also be able to detect and recognize the eggs of one or more parasites.

In some instances, the image system may also detect and recognize toxins from bacteria such as Clostridium difficile. In some instances, the image system may also detect and recognize viruses such as rotovirus.

EXAMPLES

The following examples are provided as part of the disclosure as an embodiment of the present invention. As such, none of the information provided below is to be taken as limiting the scope of the invention.

Example 1

Method of Comminuting and Analyzing a Fecal Sample for Cyclospora

Example 1 is illustrative of a preferred method of comminuting and analyzing a fecal sample for Cyclospora. The method comprises:

1) A user deposits a sample of feces in the analytical toilet into the first drain.
2) A cover is moved over the drain and high pressure jets of water are sprayed onto the sample of feces for a period of 15 seconds.
3) The feces is further comminuted using an auger with tube diameter of 30 mm and screw diameter of 28 mm rotating at a speed of 20 revolutions/min for a period of 1 min.
4) The comminuted feces passes through a second drain and a No. 50 mesh filter.
5) The comminuted feces that passes through the mesh filter is transferred to chamber through a microfluidic channel where two drops of the filtered feces sample is placed on a glass slide and dried at 60° C. using a slide warmer until the sample is dry.
6) One ml of absolute methanol is added to the dried feces sample and allowed to mix for 30 seconds.
7) One drop of Kinyoun's carbol fuchsin (Sigma Aldrich, St. Louis, Mo., USA) is added and allowed to stain for one minute. The sample is rinsed with 10 ml of distilled water and drained.
8) Two drops of destain using acid alcohol (from a mixture of 10 ml $H_2SO_4$+90 ml of absolute ethanol) is added and allowed to stand for 2 min followed by rinsing with 10 ml of distilled water.
9) One drop of malachite green is added is added to the sample and allowed to stand for 2 min followed by rinsing with 10 ml of distilled water.
10) The sample is allowed to dry on the slide using a slide warmer at 60° C. for 5 min.
11) The sample is examined using an imaging system with 40× magnification.

12) After examination of the stained fecal sample, 10 ml of 1M $H_2SO_4$ is added and allowed to soak for 2 min followed by washing with 20 ml of distilled water and drain to a sewer.

Example 2

Method of Comminuting and Analyzing a Fecal Sample for Cryptosporidia

Example 2 is illustrative of a preferred method of comminuting and analyzing a fecal sample for Cryptosporidia. The method comprises:
1) A user deposits a sample of feces in the analytical toilet into the first drain.
2) A cover is moved over the drain and high pressure jets of water are sprayed onto the sample of feces for a period of 15 seconds.
3) The feces is further comminuted using a high frequency (54 MHz) bulk acoustic wave (BAW) actuator for a period of 1 min.
4) The comminuted feces passes through a second drain and a No. 50 mesh filter.
5) The comminuted feces that passes through the mesh filter is transferred to chamber through a microfluidic channel where two drops of the filtered feces sample is placed on a glass slide and dried at 60° C. using a slide warmer until the sample is dry.
6) Two drops of acid alcohol (from mixture of 3% HCl in methanol) is added and allowed to stand for 5 min followed by rinsing with 10 ml of distilled water.
7) Two ml of boiling safranin stain (Sigma Aldrich, St. Louis, Mo., USA) is added to the sample and allowed to soak for 2 min followed by rinsing with 10 ml of distilled water.
8) One drop of malachite green is added is added to the sample and allowed to stand for 2 min followed by rinsing with 10 ml of distilled water.
9) The sample is allowed to dry on the slide using a slide warmer at 60° C. for 5 min.
10) The sample is examined using an imaging system with 40× magnification.
11) After examination of the stained fecal sample, 10 ml of 1M $H_2SO_4$ is added and allowed to soak for 2 min followed by washing with 20 ml of distilled water and drain to a sewer.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet comprising:
   a bowl for collecting feces from a user;
   a comminutor that comminutes at least a portion of the feces;
   a processing fluid driver that causes a processing fluid to mix with and transport at least a portion of the comminuted feces to an analytical station in the toilet;
   a separator that separates a sample of the at least a portion of the comminuted feces to be analyzed; and
   a wash fluid driver that causes a wash fluid to wash the feces out of the bowl.

2. The analytical toilet of claim 1, wherein the processing fluid driver comprises a fluid jet, nozzle, microfluidic, capillary, diaphragm, piston, screw, rotary, or peristaltic dispensing system.

3. The analytical toilet of claim 1, further comprising a cover that separates the comminutor from the bowl.

4. The analytical toilet of claim 1, further comprising a filter between the comminutor and the analytical station.

5. The analytical toilet of claim 4, wherein the filter comprises a disk filter.

6. The analytical toilet of claim 4, wherein the sample is moved to the analytical station through a microfluidic channel.

7. The analytical toilet of claim 1, wherein the comminutor is selected from the group consisting of an auger, an emulsifier, a masticator, a sonicator, a homogenizer, high pressure fluid, a mill, blender, Dounce homogenizer, Potter-Elvehjem homogenizer, French press, and a grinder.

8. The analytical toilet of claim 1, wherein the processing fluid comprises water together with at least one of a buffer, a reducing agent, a protease inhibitor, an osmolyte, an ionic stabilizer, and an α-helix stabilizer.

9. The analytical toilet of claim 1, wherein the separator comprises a pipette.

10. The analytical toilet of claim 1, further comprising an imaging sensor for capturing images of the comminuted feces.

11. The analytical toilet of claim 10, further comprising a channel through which a portion of the comminuted feces passes, thereby producing a thin layer of comminuted feces, and wherein the imaging sensor is on one side of the thin layer of comminuted feces and a light source is on the other side of the thin layer of comminuted feces.

12. The analytical toilet of claim 10, further comprises a processor that processes images captured by the imaging sensor to thereby recognize parasites, parasite larva, parasite eggs, bacteria or viruses.

13. The analytical toilet of claim 12, wherein the processor is capable of recognizing images of one or more of cryptosporidium, microsporidia, and isospora, tapeworms, flukes, Fasciolopsis buski, hookworms, microsporidia, whipworms, protozoa, Balantidium coli, Dientamoeba fragilis, Encephalitozoon hellem, Necator americanus, heterophyes heterophyes, Metagonimus yokogawai, pinworms, trichinosis worms, Giardia intestinalis, Giardia lamblia, Entamoeba histolytica, Cyclospora cayetanenensis, ascarias lumbricoides, strongyloidiasis, Ancylostoma duodenale, Taenia, Cystoisospora belli, Diphyllobothrium, Hymenolepsis, Echinococcus, Dipylidium, Spirometra, Enterobius vermicularis, and Cryptosporidium.

14. The analytical toilet of claim 1, wherein the analytical station comprises a slide warmer.

15. The analytical toilet of claim 1, wherein the analytical station comprises a dispenser that dispenses a stain, a fixative, a reagent, or combinations thereof.

16. The analytical toilet of claim 15, wherein the one or more stains comprise eosin/saline, acridine orange, auramine phenol, Field's stain solution A and B, Giemsa stain, Lugol's iodine, iron haematoxylin solution A and B, trichrome for microsporidia, trichrome for protozoa, malachite green, methylene blue, Gram's fuchsin, safranin O, Gram's iodine, crystal violet, or Kinyoun's Carbol fuchsin.

17. An analytical toilet for collecting, analyzing, and disposing of feces comprising:
   a bowl for collecting feces from a user;

a source of acoustic energy directed at the feces and having sufficient intensity to comminute the feces to an extent sufficient to produce comminuted feces; and a source of flush water to wash the comminuted feces out of the bowl.

18. The analytical toilet of claim 17, further comprising an imaging sensor for capturing images of the comminuted feces.

19. The analytical toilet of claim 18, further comprising a channel through which a portion of the comminuted feces passes, thereby producing a thin layer of comminuted feces, and wherein the imaging sensor is on one side of the thin layer of comminuted feces and a light source is on the other side of the thin layer of comminuted feces.

20. The analytical toilet of claim 17, further comprising a processor for processing images from the imaging sensor, and thereby recognize images of one or more parasites.

* * * * *